United States Patent
Perry

(10) Patent No.: US 9,456,609 B2
(45) Date of Patent: Oct. 4, 2016

(54) HYDROCARBONS AND METALS INDUCE BIO-CATALYST TO MODIFY DEVELOPMENT PROCESS IN PLANTS AND FRUITS

(71) Applicant: Guenevere Diane Perry, Albany, GA (US)

(72) Inventor: Guenevere Diane Perry, Albany, GA (US)

( * ) Notice: Subject to any disclaimer, the term of this patent is extended or adjusted under 35 U.S.C. 154(b) by 0 days.

(21) Appl. No.: 14/334,392

(22) Filed: Jul. 17, 2014

(65) Prior Publication Data

US 2014/0329680 A1 Nov. 6, 2014

(51) Int. Cl.
*A01N 63/02* (2006.01)

(52) U.S. Cl.
CPC ...................... *A01N 63/02* (2013.01)

(58) Field of Classification Search
None
See application file for complete search history.

(56) References Cited

U.S. PATENT DOCUMENTS

| | | | | |
|---|---|---|---|---|
| 4,432,998 A * | 2/1984 | Peer | A23C 9/1234 | 426/34 |
| 5,674,701 A * | 10/1997 | Ecker | A01H 1/04 | 435/32 |
| 8,389,441 B2 * | 3/2013 | Pierce | A01H 3/00 | 435/252.1 |
| 8,677,685 B2 * | 3/2014 | Kao | A01G 31/02 | 47/62 R |
| 2013/0341226 A1 * | 12/2013 | deHaan | A01G 9/00 | 206/423 |
| 2015/0101376 A1 * | 4/2015 | Lehtonen | C05C 3/00 | 71/22 |

FOREIGN PATENT DOCUMENTS

CN 102219602 * 10/2011

OTHER PUBLICATIONS

Allen et al., Identification and Characterization of Expoxide Carboxylase Activity in Cell Extracts of Nocardia corallina B276, Journal of Bacteriology, Apr. 1998, 180(8), 2072-8.*
Ahemad et al., Mechanism and applications of plant growth promoting rhizobacteria: Current prespective, Journal of King Saud University—Science, 2014, 26 pp. 1-20.*
Rust et al., Hydrogen cynaide sensitivity in bacterial pathogens of cyanogenic and non cyanogenic plants, Phytopathology, 1980, 70(10), 1005-8.*
Turner et al., Ethylene-induced defoliation in Ficus species and ethylene depletion by soil bacteria in peat-amended media and in vitro, J. Amer. Soc. Hort. Sci. 113(5), 794-6, 1988.*
Zeller et al., Host-Plant Selectivity of Rhizobacteria in a Crop/Weed Model System, Sep. 2007 | Issue 9 | e846.*
Alstrom et al., Cyanide production by rhizobacteria as a possible mechanism of plant growth inhibition, Biol Fertil Soils (1989) 7:232-238.*
Allen, J. and S. Ensign. 1998. Identification and characterization of epoxide carboxylase activity in cell extracts of Nocardia coralline B276. Journal of Bacteriology, 180: 2072-2078.
Ahemad, M. and M. Kibret. 2014. Mechanisms and applications of plant growth promoting rhizobacteria: Current perspective. Journal of King Saud University-Science. 20: 1-20.

* cited by examiner

*Primary Examiner* — Alton Pryor

(57) ABSTRACT

The invention is directed to methods of modifying the plant development process comprising of exposing a plant or plant part to volatiles biosynthesized by one or more bacteria or enzymes. Specifically, the embodiment uses one or more bacteria selected from the plant growth promoting bacteria group consisting of *Rhodococcus* spp., *Pseudomonas* spp., or *Xanthobacter* spp., or a mixture thereof. A closed apparatus, FIG. 1A, containing a tri-phasic system is used to expose the bacteria to hydrocarbons, iron, cyanide, and/or ammonium compounds; the method induces the biocatalyst to biosynthesize volatile compound(s) that deter ethylene production in climacteric plants or fruit resulting in the biocatalyst ability to delay fruit ripening.

15 Claims, 2 Drawing Sheets

__US 9,456,609 B2__

HYDROCARBONS AND METALS INDUCE BIO-CATALYST TO MODIFY DEVELOPMENT PROCESS IN PLANTS AND FRUITS

FIELD OF INVENTION

The present invention is in the field of post-harvest biotechnology. The invention generally relates to the method of exposing plant or plant parts to one or more bacteria that release volatile compounds, specifically to the bacteria ability to deter ethylene production and delay fruit ripening in climacteric plants or fruit.

The projected rise in global population raises concerns about the effectiveness of current agricultural techniques to meet the continuously growing demands for food, (Trostle and Seeley, 2013). Plant growth promoting bacteria (PGPB) may be a low cost and efficient tool to increase agricultural productivity and deter post-harvest loss. PGPB have also been used as biological fertilizers, biological pesticides, and biocatalyst to prevent post-harvest loss, (Ahemad and Kibret, 2014; Bashan 1998; Pierce et al., 2011; Perry, 2011). Several species of PGPB including *Azobacter, Bacillus, Azosprillum, Acetobacter, Pseudomonas*, and *Rhodococcus* species these bacteria have been used for centuries as bacterial inoculants to modify plant development and improve nutrient uptake for plant cells, (Bashan, 1998; Vacheron et al., 2013). Ethylene production regulates plant development in climacteric fruit. Controlling ethylene concentrations can deter the plant development process and retard fruit ripening, (Binder et al., 2004; Burg, 1973; Trobacher, 2009; Victor et al., 2012; Yip and Yang, 1988; Yang and Oetiker, 1998). PGPB modify plant development by degrading ethylene, degrading ethylene precursors, and/or producing compounds that inhibit auxin production in plant cells, (Allen and Ensign, 1998; Arshad et al., 2007; DeBont and Albers, 1976; Dhungana et al., 2007; Elsgaard, 1998; Glick, 2012; Kloepper et al., 1991; Penrose and Glick, 2003). Plant growth promoting bacteria can also use dehydratase and nitrile degrading enzymes to biosynthesize cyanohydrins or auxins that manipulate the plant development process, (Egamberdieva, 2012; Hayat et al., 2010; Nomura et al., 2012; Kato et al., 2004).

A previous method to induce bacteria to delay fruit ripening was developed by Pierce et al., 2011 and U.S. patent 2013/0274, 102 (2013). Bacteria were induced to delay fruit ripening after prolonged exposure to cobalt, urea, and/or asparagine. The cell paste was immobilized on cellulose material and placed on or near fruit to delay climacteric ripening. This method was arduous and laborious; the induction process lasted for a 13-14 day period. This method would be very costly to translate into actual manufacturing and industrial applications. The multiple culture steps, expensive equipment, and expensive materials, including urea and glucose, would drive-up production cost and reduce profits.

The patentable method exposes bacteria to a single required inducer a short chained hydrocarbon, specifically ethylene and/or propylene. Secondary inducers iron and ammonium compounds enhance the bacteria production of nitrile compounds that delay fruit ripening. This method requires less media, reduced production time, and increased reproducibility of results, improving the inventions relevance for industrial and manufacturing applications. Biocatalyst exposed to inducers were able to modify the plant development process and delay the effects of fruit ripening, including changes in hue, texture, firmness, reduced presence of brown spotting, and reduced fungal infection.

BRIEF SUMMARY OF INVENTION

In accordance with one embodiment, the new method is directed to the use of short chain hydrocarbons, including but not limited to propylene (propene) and/or ethylene to induce PGPB. The additional necessary media components include heavy metals, including but not limited to iron, and ammonium compounds to induce biocatalyst ability to modify plant development in climacteric fruit.

The PGPB are referred to as a biocatalyst comprising of one or more bacteria, particularly *Rhodococcus* or *Norcardia* spp., or a mixture thereof. The biocatalyst, comprising of PGPB include but is not limited to *Acetobacter, Azobacter, Azosprillum, Bacillus, Brevibacterium, Norcardia, Pseudomonas, Rhodococcus*, or *Xanthobacter* spp. that can catalyze the hydrocarbon into volatile compounds that deter ethylene production in climacteric plants or fruit.

The present new invention method occurs wherein the biocatalyst are cultivated in a closed tri-phasic system apparatus described herein. This invention further provides an apparatus used to facilitate the induction of PGPB to produce volatile compounds required to modify the plant development process and delay ripening in climacteric plants or fruit.

BRIEF DESCRIPTION OF THE DRAWINGS

The invention was described above in broad terms, reference will now address the accompanying drawing, this drawing is not necessarily drawn to scale, and wherein.

DETAILED DESCRIPTION

Figure 1A:
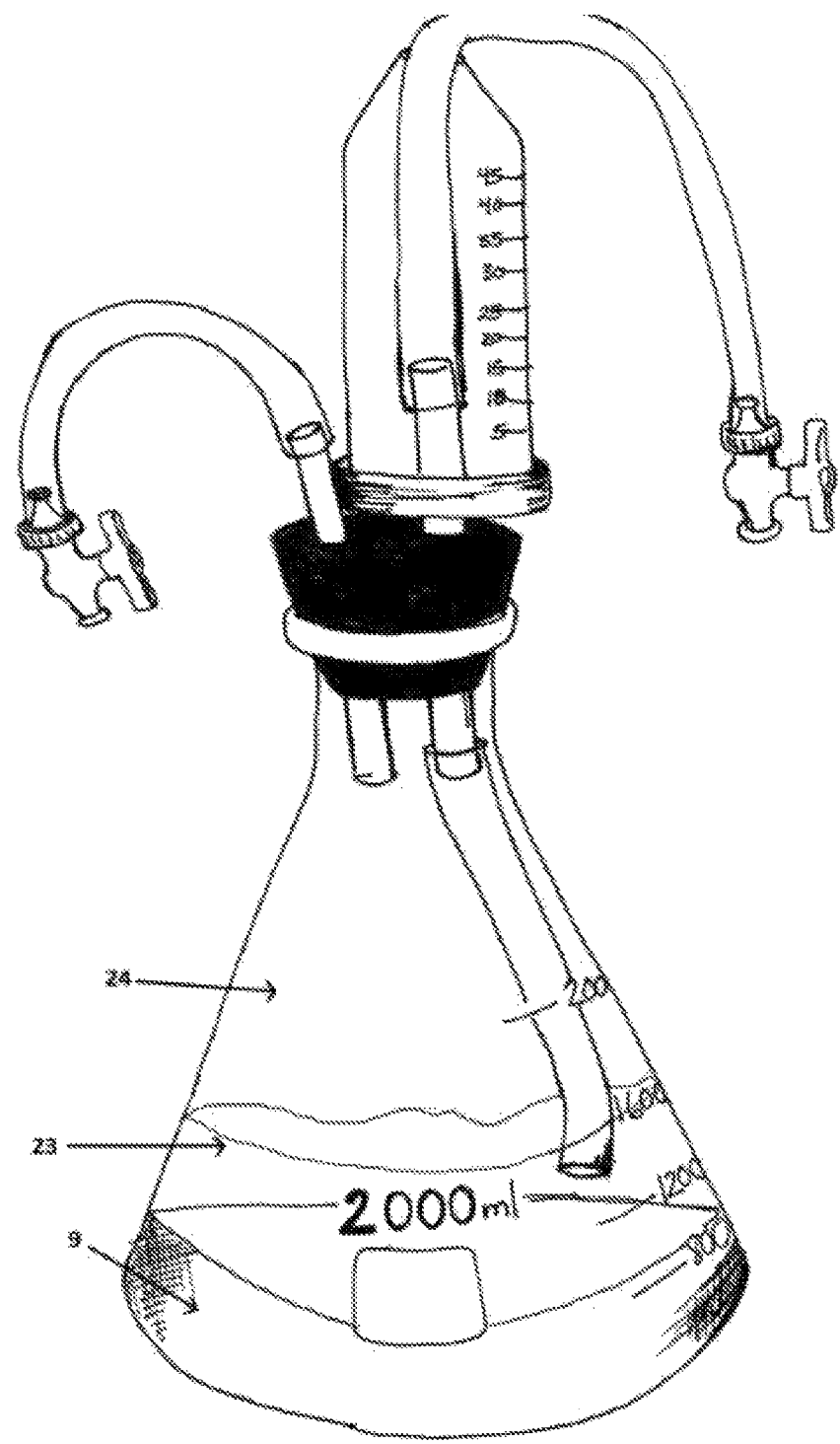
FIG. 1A is a perspective front view of the apparatus of the past invention; the apparatus contains a tri-phasic system comprised of a solid, liquid, and gaseous phase labeled 9, 23, and 24 respectively.
Figure 1B:
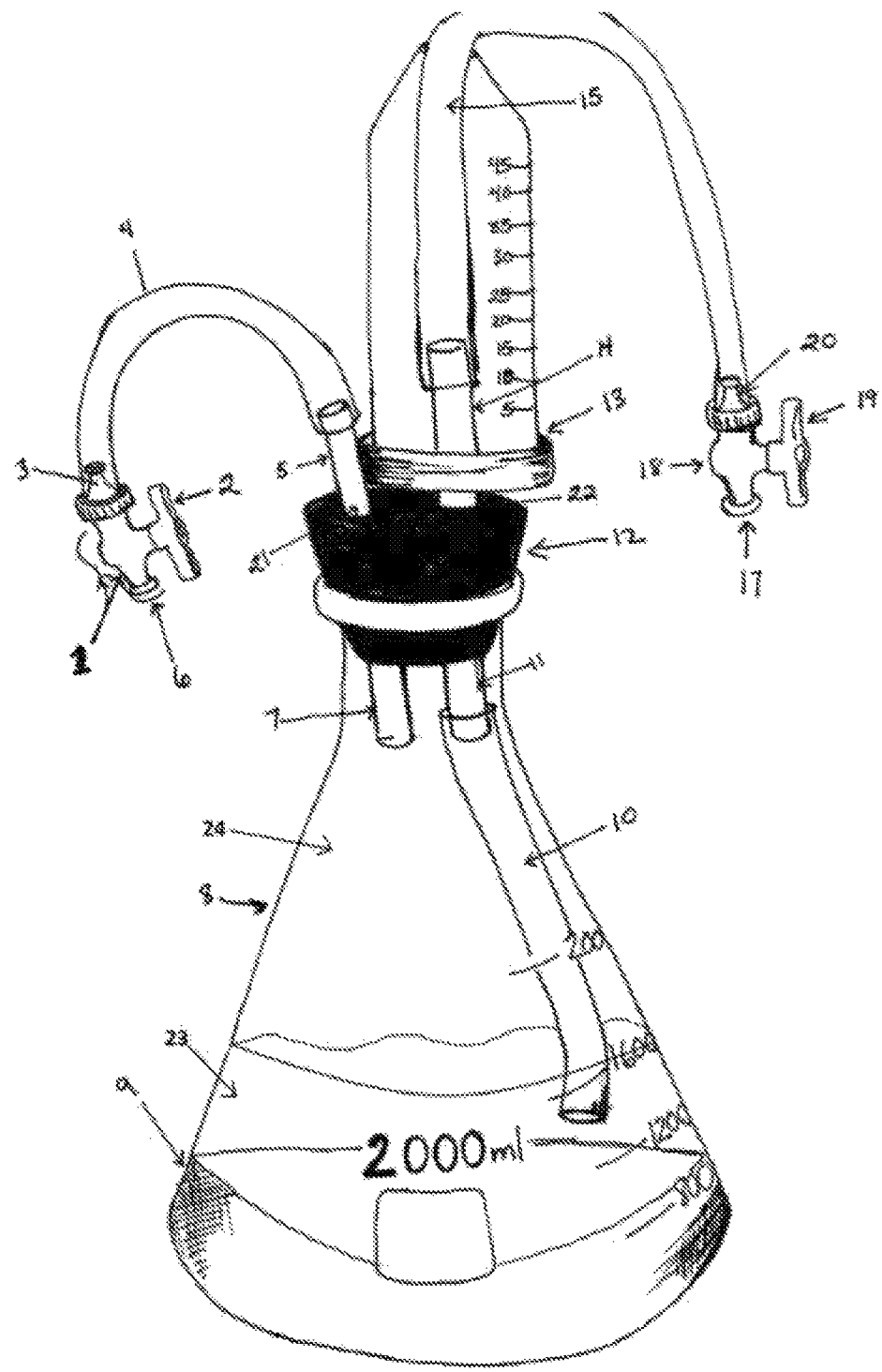
FIG. 1B is a detailed operational view of the proportion indicated by the section lines 2-3 in FIG. 1, a closed system apparatus of the present invention; the apparatus contains a tri-phasic system. The biocatalyst is maintained in the solid and liquid phase of the system as defined herein below, and comprises one or more of the microorganism of the invention.

FIGS. 1A and 1B—First Embodiment

The inventor has discovered a method to induce plant growth promoting bacteria to perform as a biocatalyst that are capable of converting short chained hydrocarbons into volatile compounds that manipulate the plant development process and delay fruit ripening. This detailed description should not be considered a means of limiting this invention to a particular embodiment. The description contains the word "comprising", or grammatical variations of the word, it is understood to imply inclusion rather than limitations. The one or more bacteria used in the methods and apparatuses of the invention may at times be more generally referred to herein as the "biocatalyst." The hydrocarbons are aliphatic gaseous compounds, including but not limited to propylene (propene) and/or ethylene compound or mixture thereof. The volatile compounds produced from the reaction, include but are not limited to nitriles and/or cyanohydrin mixture or combination thereof. The bacteria also uptake additional compounds released by plant cells during the induction process, including cyanide. The induction process also induces and stabilizes several enzymes found in *Rhodococcus* or *Norcardia*, including but not limited to nitrile degrading enzymes and/or monooxygenase or a combination thereof within the bacteria. The present invention is described in full detail herein after; references are made to embodiments included in this application.

Elements to monitor the efficiency of the biocatalyst can be attached to the apparatus to monitor carbon dioxide levels or pH levels in the media. Conversion of hydrocarbons to volatile compounds in a biocatalyst may comprise of additional features to permit continued circulation of air flow within the closed system. An individual skilled in the art could envision modifications for the apparatus to improve monitoring and controlling of the atmospheric conditions for the biocatalyst.

One embodiment of the closure is illustrated in FIG. 1A (front view) and FIG. 1B (detailed operational view). In particular embodiments of the invention the biocatalyst are cultivated in a closed flask container, providing a closed system. For example, as shown in FIG. 1A, the apparatus contains a tri-phasic system comprised of a solid, liquid, and gaseous phase. The solid phase (9) is comprised of 12 g of Bacto agar suspended into 300 ml of $dH_2O$, autoclaved and cooled in a 2 L Erlenmeyer flask. However the solid phase can consist of any of a gelatinous structure, bead-like structure, and/or a matrix like structure that can support microbial cells and facilitate filamentous growth. The liquid phase (23) contains 300 ml of the induction media that consist of a heavy metal, ammonium chloride, and phosphate compounds. The gaseous headspace (24) was filled with 10-15% of hydrocarbon gas for 3-5 days at 30° C. and 120 rpm. The gaseous compounds can include ethylene and/or propylene.

OPERATION

First Embodiment FIG. 1B

A detailed operational view of the apparatus used for the cultivation of biocatalyst, shown in FIG. 1B. The apparatus is 2 L Erlenmeyer flask (8), apparatus could consist of any closed system container that could support a tri-phasic system. The rubber stopper (12) prevented loss of gaseous media components. The agar base (9) provides a solid surface for biofilm formation; the solid phase is an essential component to enhancing bacteria ability to modify plant development. The liquid phase (23) contains induction media necessary to induce bacteria ability to modify plant development. The gaseous headspace (24) contains hydrocarbon gas, an essential inducer to enhance bacteria ability to modify plant development.

Headspace Collection—FIG. 1B

Gaseous components are added and removed from the headspace using a two way valve (1). The open/close flow and direction of the valve is controlled by knob (2). The entry port (6) is used to attach syringes to inject gas into the system, media or gas enters the connecting tubing through the exit port (3). The 3/16 inch rubber tubing (4), is used throughout the system, the tubing is flexible and autoclavable. Cells pass quickly through the rubber tubing with little resistance or backflow. The rubber tube is connected to ⅛ silicon tube (5), silicon is rigid and necessary for constructing entry and exit point through the holes (21) in the rubber stopper. Gas enters the headspace (7).

Sample Collection—FIG. 1B

Gaseous and liquid components are added and removed through a two way valve (18). The open/close flow and direction of the valve is controlled by knob (19). The entry port (17) is used to attach syringes to inject liquid media into the system, enters the connecting tubing through the exit port (20). The 3/16 inch rubber tubing (15) is used throughout the system. The rubber passes into a 50 ml falcon tube (13) and is loosely connected to ⅛ silicon tube (14). The falcon tube (13) acts as a reservoir for over flow during cultivation, exposed openings are sealed with silicon based epoxy. The ⅛ silicon tube (14) are inserted into the stopper hole (22). A portion of the silicon tubing enters the flask (11) and connects to 3/16 inch rubber tubing (10). The rubber tubing is perforated on the ends and slightly coiled into the medium to allow for direct bubbling of gaseous components into the medium.

The present invention is generated in a closed system apparatus, comprising of a tri-phasic media condition. The tri-phasic condition consist of a solid porous base, aqueous phase, and a gaseous phase composed of a hydrocarbon and air mixture. The mechanism used for induction of the biocatalyst is not intended to be limiting by a particular enzyme, but may increase activity or expression of one or more enzymes, comprising of dehydratase, nitrile degrading enzyme, and/or monooxygenase, or a mixture thereof.

The induction of one or more of these enzymes may play a role conversion of a hydrocarbon to a volatile compound by the biocatalyst. This present invention encompasses biocatalysts that produce, or are induced to produce, or are genetically modified to produce dehydratase, nitrile degrading, and/or monooxygenase enzyme, at a quantity or at an enzymatic activity level sufficient for the conversion of short chained hydrocarbons to volatile compounds that deter ethylene production in climacteric plants or fruit. These enzymes have been studied in depth in literature based publications, possessing recognized enzymatic activities. The abundance of reference material related to the enzymes assures that such enzymes are well known to individuals skilled in the art, and the enzymes discussed in this invention can be easily produced, engineered, or purified from the biocatalyst.

The following embodiments are offered as examples, and are felt to be non-limiting and are meant to illustrate the invention but are not meant to be limiting in any way.

EXAMPLES

*Rhodococcus* cells were suspended in the induction media and exposed to the hydrocarbons for 3-5 days at 30° C. and 120 rpm. Biocatalyst exposed to the induction media were able to modify plant development process, and delaying ripening in climacteric plants and fruit.

TABLE 1

| Induction Media | |
|---|---|
| M9 Stock Media (autoclaved) | |
| $Na_2HPO_4$—$7H_2O$ | 64 g/L |
| $KH_2PO_4$ | 15 g/L |
| NaCl | 2.5 g/L |
| $NH_4Cl$ | 5.0 g/L-6.0 g/L |
| $dH_2O$ | 1 L |
| Working Solution M9 Media (Sterile) | |
| M9 media | 200 ml |
| 1M $MgSO_4$ (sterile) | 2 ml |
| 1M $CaCl_2$ (sterile) | 100 µl |

TABLE 1-continued

| Induction Media | |
|---|---|
| Propylene and/or Ethylene (v/v) | (10-15%) |
| Cobalt or Iron | 0.201 g/L |

Table 1: Media contained ammonium chloride and heavy metals induced bacteria to delay fruit ripening.

Fruit were collected from experiments, a Brix measurement were determined stages to validate that fruit stored with biocatalyst ripening process was delayed compared to control samples. °Brix (U) measures physiological changes, such as changes in soluble carbohydrate concentrations. Brix (U) increase and continue to increase throughout the ripening process.

TABLE 2

| Brix Measurements | | | |
|---|---|---|---|
| | Control | Cobalt & Urea | Cobalt, Urea, & Propylene |
| Brix° Unit (% Sugar Content) | 15 ± 0.50 | 13 ± 1.5 | 10 ± 1.2 |

Table 2: Brix° (U) measurement determines % of soluble sugars from apple samples. Apples were incubated with live biocatalyst for 12 days at 21° C. Control initial measurement ~9° (U) Brix.

Exposure to hydrocarbons induced nitrile degrading activity in *Rhodococcus* cells. Increased nitrile degrading activity suggests bacteria cells converted hydrocarbons into volatile compounds.

TABLE 3

| Nitrile Degrading Activity | | | | |
|---|---|---|---|---|
| Carbon Source | Inducers | Substrate | Post Induction Δ(U) | Post Fruit Exposure Δ(U) |
| Glucose | N.A. | Acrylonitrile$_{(1\,g/L)}$ | 2 ± 4.3 | 4 ± 0.7 |
| | | *Cyanide$_{(0.05\,g/L)}$ | N.D. | 2.0 ± 0.6 |
| Glucose | Cobalt, Urea | Acrylonitrile$_{(1\,g/L)}$ | 41 ± 11 | 55 ± 1.0 |
| | | *Cyanide$_{(0.05\,g/L)}$ | 1 ± 0.0 | 3 ± 0.3 |
| Propylene | Propylene | Acrylonitrile$_{(1\,g/L)}$ | 27 ± 2.0 | 48 ± 10.5 |
| | | *Cyanide$_{(0.05\,g/L)}$ | 1.0 ± 0.0 | 3.0 ± 0.3 |
| Propylene | Propylene, Cobalt, Urea | Acrylonitrile$_{(1\,g/L)}$ | 75 ± 23 | 96 ± 17 |
| | | *Cyanide$_{(0.05\,g/L)}$ | 5.30 ± 3.0 | 4.0 ± 1.2 |

Table 3: *Rhodococcus rhodochrous* DAP 96253 cultured in tri-phasic conditions. Nitrile degrading assay measures (U) units of activity. Units 1 uM of acrylonitrile converted to 1 uM acrylamide in 1 min, pH 7.2 at 30° C.
*Units 1 uM of KCN converted to 1 uM formic acid in 1 min, pH 7.2 at 30° C.
N.D. = Not Detected;
N.A. = No Addition

CONCLUSION, RAMIFICATIONS, AND SCOPE

The process (method) to induce bacteria with a hydrocarbon that results in the biosynthesis of a natural nitrile compound that can delay fruit ripening can have global implications and numerous applications. While the above description contains many specifications, these should not be construed as limitations on the scope of any embodiment, but as exemplifications of the presently preferred embodiments thereof. Many other ramifications and variations are possible within the teachings of various embodiments. For example, the heavy metals used in this experiment can include iron or cobalt as secondary cofactors to enhance bacteria and enzyme yield and increase product efficacy. Both metals can induce enzymatic activity to produce volatile compounds required to delay fruit ripening, but enzyme activity varies in the presence of iron verses the presence of cobalt.

Thus the scope of the invention should be determined by the appended claims and their legal equivalents, and not by the given examples.

The invention claimed is:

1. A method for inducing bacteria in a tri-phasic condition to biosynthesize volatile compounds that deter ethylene production in climacteric plant cells; wherein the reduction of ethylene production resulting in the delay of the ripening process in climacteric fruit or plants; wherein the method comprises of exposing plant or plant parts to exogenous volatiles released by one or more bacteria, wherein the biosynthesized volatile compounds are induced by exposure of the bacteria to inducing agents including short chained hydrocarbons comprising of propylene and/or ethylene, and optionally a nitrogen compound comprising urea, ammonium sulfate, or cyanide, and mixtures thereof, and wherein the one or more bacteria produce said volatile compounds upon exposure to the plant or plant part to delay the plant development.

2. The method of claim 1, wherein the one or more bacteria are selected from a group consisting of *Rhodococcus* spp., *Pseudomonas* spp., and *Xanthobacter* spp.

3. The method of claim 2, wherein the *Rhodococcus* spp. includes *Rhodococcus rhodochrous* strain DAP 96253 strain, *Rhodococcus* sp. strain DAP 96622, *Rhodococcus erythropolis*, or mixtures thereof.

4. The method of claim 1, wherein the one or more bacteria are induced by exposure to a short chained hydrocarbon, iron, cyanide, and/or ammonium compound.

5. The method of claim 4, wherein the short chained hydrocarbon consisting of ethylene and/or propylene (propene).

6. The method of claim 1, wherein the volatile compound produced by the one or more bacteria includes an aliphatic nitrile, ethylene cyanohydrin, and/or propylene cyanohydrin or mixture thereof.

7. The method of claim 1, wherein the plant or plant part is directly or indirectly exposed to the nitrile compound produced by the one or more bacteria.

8. The method of claim 1, wherein inducers are coupled with cofactors comprising of iron and ammonium compounds or a mixture thereof to enhance bacteria biomass.

9. The method of claim 1, wherein the plant part is a fruit, a vegetable, or a flower.

10. The method of claim 8, wherein the fruit is climacteric fruit.

11. The method of claim 8, wherein the plant is non-climacteric fruit.

12. The method of claim 1, wherein the plant part is a flower and the delay in plant development includes developmental changes to the flower and stem structural appendages.

13. The method of claim 11, wherein the flower appendages include petals and leaves.

14. The method of claim 1, wherein the one or more bacteria are suspended in an aqueous solution and are placed in, placed on, or submerged below a physical structure suitable for transport or storage of the plant or plant part.

15. A method for modulating ethylene production in plant cells indirectly regulating plant cells during late stage development which comprises exposing a plant or plant part to exogenous volatile compound(s) biosynthesized by enzymatic extract of one or more bacteria, wherein volatiles are biosynthesized upon bacteria exposure in a triphasic condition to inducing agents comprising short chained hydrocarbons including propylene and/or ethylene, and optionally a nitrogen compound comprising of urea, ammonium sulfate, or cyanide, and mixtures thereof, and wherein the extract of said bacteria produce said volatile compounds in the triphasic condition upon exposure to the plant or plant part to delay the plant development.

* * * * *